(12) United States Patent
Roney, Jr. et al.

(10) Patent No.: US 7,717,666 B2
(45) Date of Patent: May 18, 2010

(54) METHODS AND APPARATUS FOR ROTARY MACHINERY INSPECTION

(75) Inventors: Robert Martin Roney, Jr., Schoharie, NY (US); Richard Michael Hatley, Convent Station, NJ (US)

(73) Assignee: General Electric Company, Schenectady, NY (US)

( * ) Notice: Subject to any disclaimer, the term of this patent is extended or adjusted under 35 U.S.C. 154(b) by 554 days.

(21) Appl. No.: 11/255,716

(22) Filed: Oct. 21, 2005

(65) Prior Publication Data

US 2007/0089545 A1 Apr. 26, 2007

(51) Int. Cl.
*F04D 29/00* (2006.01)
(52) U.S. Cl. .......................................... 415/1; 415/118
(58) Field of Classification Search ................. 415/118; 324/228–243; 416/61; 600/104, 106, 109, 600/137, 138, 139, 141, 143, 146; 356/241.1–241.6
See application file for complete search history.

(56) References Cited

U.S. PATENT DOCUMENTS

| | | | | |
|---|---|---|---|---|
| 4,412,177 A * | 10/1983 | Petrini et al. | ................ | 324/226 |
| 4,889,000 A | 12/1989 | Jaafar et al. | | |
| 4,970,890 A | 11/1990 | Jaafar et al. | | |
| 5,105,658 A | 4/1992 | Jaafar et al. | | |
| 5,314,445 A * | 5/1994 | Heidmueller nee Degwitz et al. | ......................... | 606/208 |
| 6,414,458 B1 * | 7/2002 | Hatley et al. | ........... | 318/568.12 |
| 6,525,500 B2 * | 2/2003 | Hatley et al. | ........... | 318/568.12 |
| 6,532,840 B2 * | 3/2003 | Hatley et al. | ................ | 73/866.5 |
| 6,695,774 B2 * | 2/2004 | Hale et al. | .................. | 600/173 |
| 6,883,527 B2 | 4/2005 | Travaly et al. | | |
| 6,899,593 B1 * | 5/2005 | Moeller et al. | .................. | 451/6 |
| 7,097,539 B2 * | 8/2006 | Moeller et al. | .................. | 451/6 |
| 7,112,118 B1 * | 9/2006 | Moeller et al. | .................. | 451/6 |
| 2002/0073788 A1 * | 6/2002 | Hatley et al. | ................ | 73/866.5 |
| 2002/0074965 A1 * | 6/2002 | Hatley et al. | ........... | 318/568.12 |
| 2002/0089298 A1 * | 7/2002 | Hatley et al. | ........... | 318/568.12 |
| 2002/0108644 A1 | 8/2002 | Hoadley et al. | | |
| 2004/0016449 A1 | 1/2004 | Travaly et al. | | |
| 2004/0074093 A1 | 4/2004 | McCarvill et al. | | |
| 2005/0073673 A1 | 4/2005 | Devitt et al. | | |
| 2005/0107001 A1 * | 5/2005 | Moeller et al. | .................. | 451/6 |
| 2005/0148287 A1 * | 7/2005 | Moeller et al. | .................. | 451/6 |
| 2006/0146127 A1 * | 7/2006 | Bagley et al. | .................. | 348/83 |
| 2006/0228993 A1 * | 10/2006 | Moeller et al. | .................. | 451/6 |
| 2006/0258265 A1 * | 11/2006 | Moeller et al. | .................. | 451/6 |

* cited by examiner

*Primary Examiner*—Edward Look
*Assistant Examiner*—Aaron R Eastman
(74) *Attorney, Agent, or Firm*—Armstrong Teasdale LLP

(57) ABSTRACT

Methods, apparatus and systems for machinery testing and inspection using a manipulator are provided. The apparatus includes a tubular shaft, an operator end coupled to the tubular shaft and including a first spool rotatably coupled to the operator end, an effector including an attachment end that includes a second spool rotatably coupled to the attachment end, and a control cable channeled through the shaft from the first spool to the second spool. The control cable is wound at least partially around the first spool and is wound at least partially around the second spool such that rotation of the first spool rotates the second spool using the control cable.

20 Claims, 4 Drawing Sheets

METHODS AND APPARATUS FOR ROTARY MACHINERY INSPECTION

BACKGROUND OF THE INVENTION

This application relates generally to gas turbine engines and, more particularly, to methods and apparatus for inspecting gas turbine engine compressor and turbine rotor assemblies.

At least some known gas turbine engines include a compressor for compressing air, which is mixed with a fuel and channeled to a combustor wherein the mixture is ignited within a combustion chamber for generating hot combustion gases. The hot combustion gases are channeled downstream to a turbine, which extracts energy from the combustion gases for powering the compressor, as well as producing useful work to propel an aircraft in flight or to power a load, such as an electrical generator.

Known compressors include a rotor assembly that includes at least one row of circumferentially spaced rotor blades. Each rotor blade includes an airfoil that includes a pressure side and a suction side connected together at leading and trailing edges. Each airfoil extends radially outward from a rotor blade platform. Each rotor blade also includes an attachment portion, such as, a dovetail that extends radially inward from the platform, and is used to mount the rotor blade within the rotor assembly to a rotor disk or spool. More specifically, at least some known rotor disks include a plurality of circumferentially spaced axially oriented dovetail slots that are sized to receive a respective one of the plurality of rotor blades therein.

During operation, the rotor blades may be subjected to environmental and loading forces that may cause in-service cracking of the blades. Known inspection techniques are limited in their ability to assess the integrity of the blades while the blades are in-place. More specifically, a visual inspection only permits a limited examination of the blades for cracks in the airfoil and in a very limited area of the dovetail. To thoroughly examine the blades where cracking may originate, at least a portion of the engine casing may need to be removed to facilitate removal of each blade, and subsequent inspection of the blades with visual, magnetic particle, or liquid penetrant techniques. However, because of labor and cost constraints such techniques may be impracticable in some instances.

BRIEF DESCRIPTION OF THE INVENTION

In one embodiment, a manipulator includes a tubular shaft, an operator end coupled to the tubular shaft and including a first spool rotatably coupled to the operator end, an effector including an attachment end that includes a second spool rotatably coupled to the attachment end, and a control cable channeled through the shaft from the first spool to the second spool. The control cable is wound at least partially around the first spool and is wound at least partially around the second spool such that rotation of the first spool rotates the second spool using the control cable.

In another embodiment, an inspection system is provided. The system includes a manipulator including a tubular shaft coupled to an operator end at a first end and coupled to an effector at a second end opposite the first end, the operator end rotatably is coupled to a first spool, the effector is rotatably coupled to a second spool, and a control cable extends slidably through the tubular shaft from the first spool to the second spool, the control cable is wound at least partially around the first spool and is wound at least partially around the second spool such that rotation of the first spool rotates the second spool using the control cable. The system further includes at least one test or inspection device coupled to the second spool.

In yet another embodiment, a method of machinery testing and inspection using a manipulator is provided. The manipulator includes an operator end coupled to a first end of a manipulator body and an attachment end coupled to a second end of the manipulator body. The method includes attaching at least one test or inspection device to the attachment end, positioning the at least one test or inspection device proximate a component to be inspected, and repositioning the at least one test or inspection device with respect to the component by controlling the operator end of the manipulator.

DETAILED DESCRIPTION OF THE INVENTION

Figure 1:
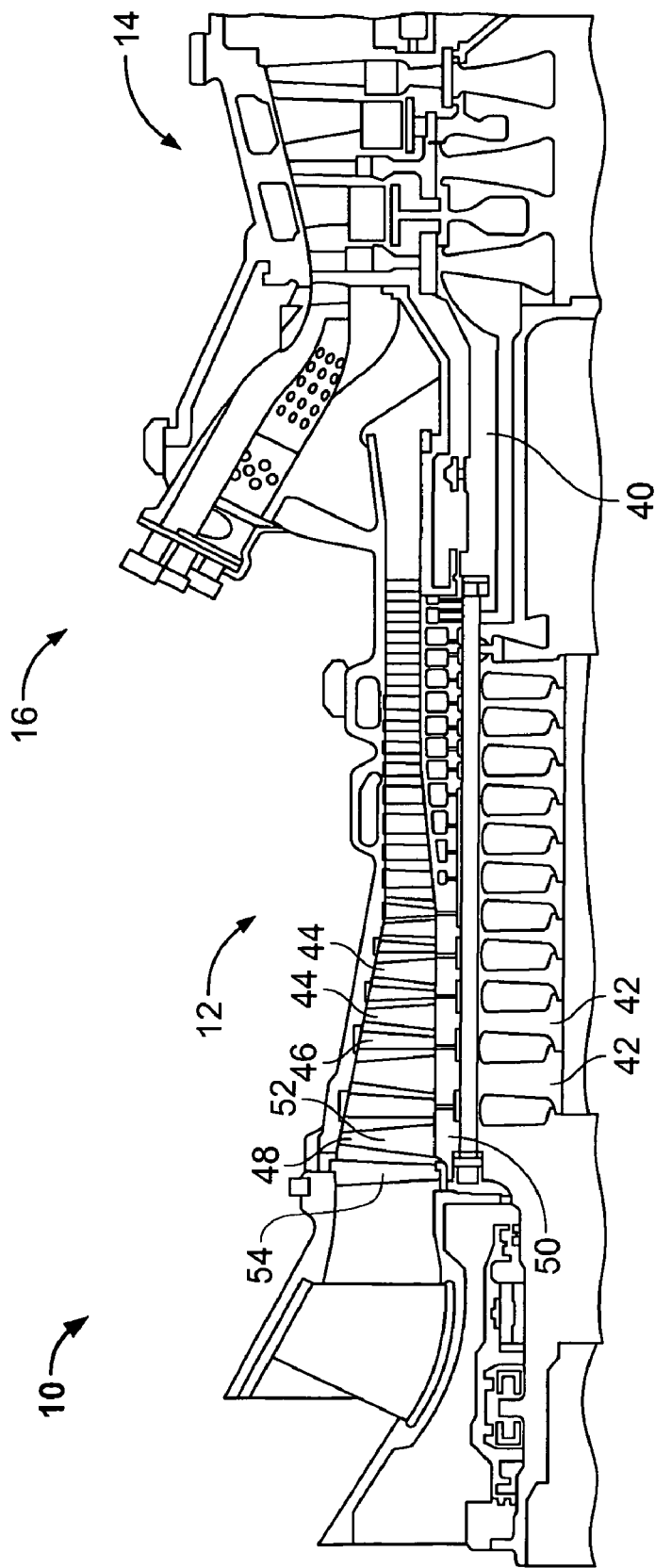
FIG. 1 is a side elevation view of an exemplary gas turbine engine.

FIG. 1 is a side elevation view of an exemplary gas turbine engine 10 that includes a compressor section 12, a turbine section 14 and a plurality of combustors 16 (only one combustor shown in FIG. 1) Engine 10 includes a rotor 40 including a plurality of rotor wheels 42. Each rotor wheel 42 is configured to mount a plurality of components, such as, but not limited to, buckets or blades 44, which in conjunction with a respective number of stator vanes 46, form the various stages of engine 10. In the exemplary embodiment, a plurality of compressor blades 44 are coupled to a first row 48 that includes a first-stage rotor wheel 50. Each blade 44 includes an airfoil 52 that is mounted in opposition to respective first-row stator vanes 54. Blades 44 are spaced circumferentially about first-stage wheel 50. Turbine engine 10 may drive a generator (not shown) for producing electrical power. In the exemplary embodiment, engine 10 is a MS6001B gas turbine engine, commercially available from General Electric Company, Greenville, S.C.

Figure 2:
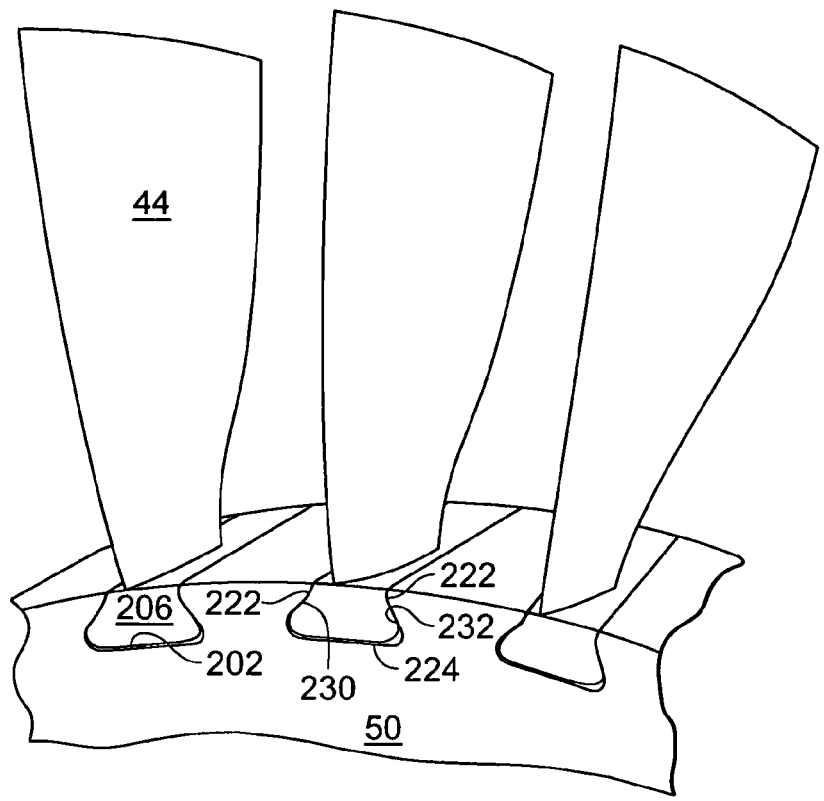
FIG. 2 is a perspective view of a portion of first stage rotor wheel that may be used with the gas turbine engine shown in FIG. 1.

FIG. 2 is a perspective view of a portion of first stage rotor wheel 50. Rotor wheel 50 includes a plurality of axially aligned dovetail slots 202 that are spaced circumferentially about a radially outer periphery of wheel 50. Slots 202 receive an attachment portion, such as a dovetail 206 of blade 44, therein. More specifically, blades 44 are removably coupled within disk slot 202 by each respective blade dovetail 206. Accordingly, slot 202 is shaped to generally complement a shape of each dovetail 206 received therein, and accordingly, in the exemplary embodiment, includes a pair of wheel post tangs 222 and a disk slot bottom 224 that extends between wheel post tangs 222. In the exemplary embodiment, disk slot 202 also includes a pair of opposed wheel faces 230 and 232.

Figure 3:
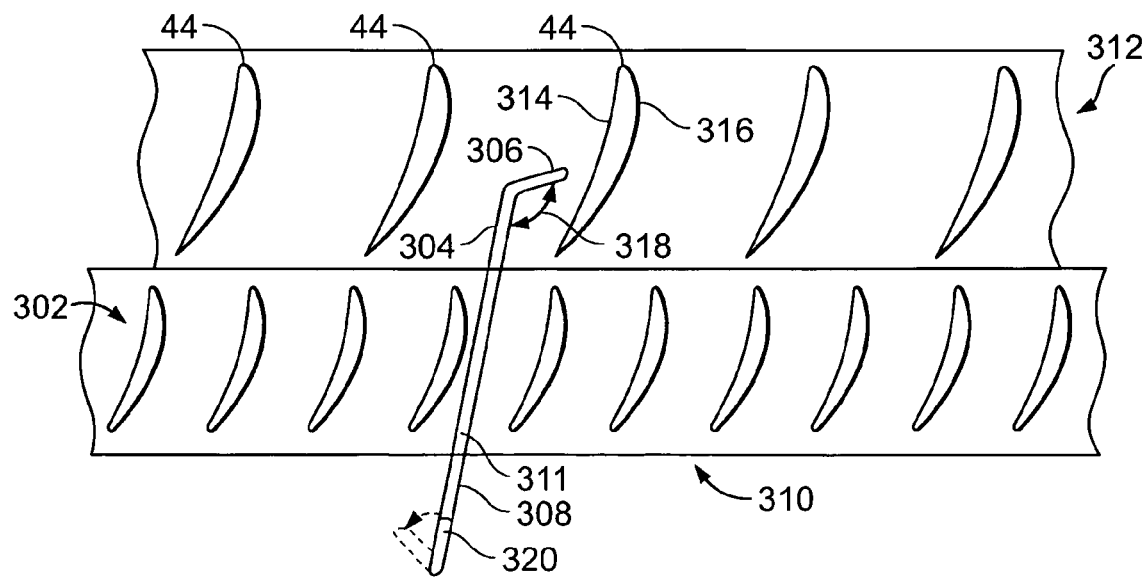
FIG. 3 is a radial perspective view of a row of inlet guide vanes (IGV) and a row of blades that may be used with the gas turbine engine shown in FIG. 1.

FIG. 3 is a radial perspective view of a row of inlet guide vanes (IGV) 302 and a row of blades 44 that may be used with gas turbine engine 10 (shown in FIG. 1). In the exemplary embodiment, a manipulator 304 is positioned with an effector 306 proximate blade 44 and an operator end 308 in an accessible area 310 upstream from inlet guide vanes 302. A manipulator shaft 311 is configured to extend between inlet guide vanes 302 to access a first row of blades 312. Manipulator shaft 311 is also configured to extend between first row of blades 312 to access a second row of blades (not shown) downstream from first row of blades 312.

Manipulator 304 is further configured to support one or more devices for testing and/or inspecting one or more of blades 44. For example, manipulator 304 may carry a borescope for visually inspecting blades 44, a test transducer, such as an ultrasound transducer, or a penetrant test assembly for sequential application of solutions used in dye penetrant testing of blades 44. Inlet guide vanes 302 may be blocked in a full open position to facilitate testing of blades 44.

In operation, manipulator 304 is positioned with effector 306 proximate a pressure side 314 or suction side 316 of blade 44. Effector 306 is variably positionable with respect to manipulator shaft 311 such that an angle 318 between manipulator shaft 311 and effector 306 is changeable based on the operation of a handle 320 located in operator end 308. In the exemplary embodiment, effector 306 is coupled to handle 320 using a control cable (not shown in FIG. 3). In an alternative embodiment, an actuator (not shown) is coupled to a controller (not shown) located on operator end 308. For example, a motor such as a servo motor may be used to change angle 318 in response to an actuation of a switch or a dial. In various embodiments, manipulator 304 is fixed to a stable support and effector 306 is moved using handle 320 to position effector 306 to perform a desired test. Additionally, manipulator 304 is hand-held and moved with respect to blade 44 to facilitate positioning effector 306 during a test or inspection.

Figure 4:
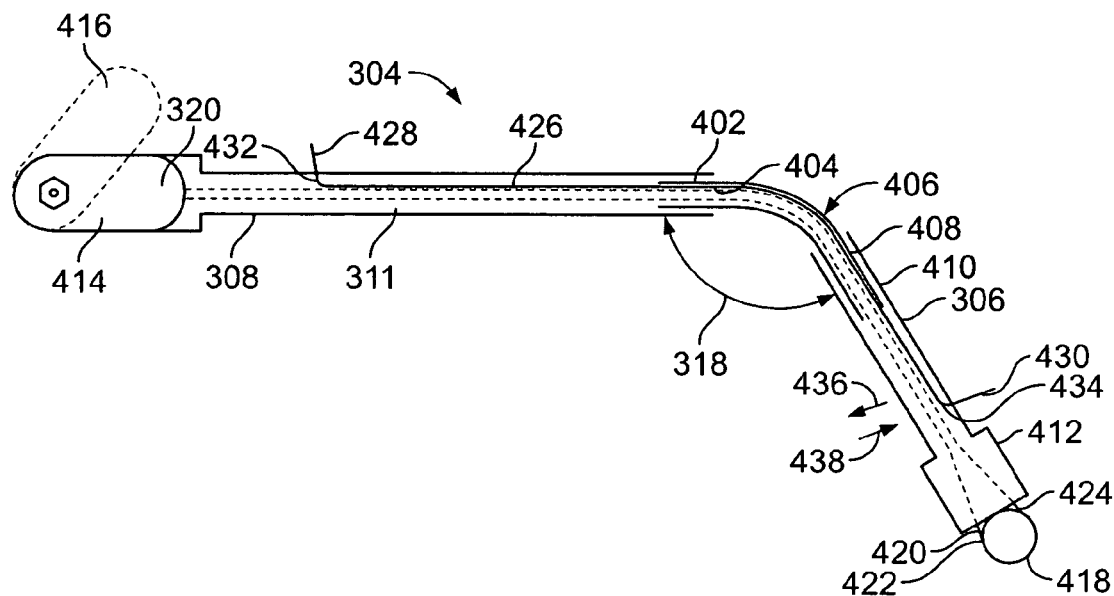
FIG. 4 is a cutaway schematic view of an exemplary embodiment of a manipulator that may be used with the gas turbine engine shown in FIG. 1.

FIG. 4 is a cutaway schematic view of an exemplary embodiment of manipulator 304 that may be used with gas turbine engine 10 (shown in FIG. 1). In the exemplary embodiment, manipulator shaft 311 is fabricated from a length of hollow tubing including operator end 308 at one end and a coupling end 402 at an opposite end. Coupling end 402 is configured to engage a first end 404 of a flexible tube 406. A second end 408 of flexible tube 406 is configured to engage a first end 410 of effector 306. In the exemplary embodiment, flexible tube 406 is resilient such that when deflected from a predetermined angle 318, flexible tube 406 tends to flex back to angle 318. Effector 306 includes an attachment end 412 opposite first end 410 that is configured to engage and retain one or more of a plurality of test and/or inspection instruments (not shown).

In the exemplary embodiment, operator end 308 includes handle 320 that is movable between a first position 414 and a second position 416. Handle 320 is coupled to a spool 418 rotatably coupled to attachment end 412. A control cable 420 extending from handle 320 is coupled to spool 418 such that manipulation of handle 320 causes a first lead 422 of control cable 420 to lengthen and a second lead 424 of control cable 420 to shorten. Control cable 420 is wound around spool 418 such that translation of control cable 420 about spool 418 causes spool 418 to rotate.

An effector control cable 426 includes a first end 428 and a second end 430. Effector control cable 426 extends from a first aperture 432 in shaft 311 to a second aperture 434 in effector 306. Second end 430 is fixed to effector 306 at second aperture 434 such that shortening effector control cable 426 at first aperture 432 pulls effector 306 toward shaft 311 causing angle 318 to change in a first direction 436. When effector control cable 426 is lengthened at first aperture 432 the resilience of tube 406 or a bias member (not shown) causes angle 318 to change in an opposite direction 438. Each length of effector control cable 426 between first aperture 432 and second aperture 434 corresponds to a different angle 318 such that manipulating the length of control cable 426 effector 306 to change position with respect to shaft 311.

Figure 5:
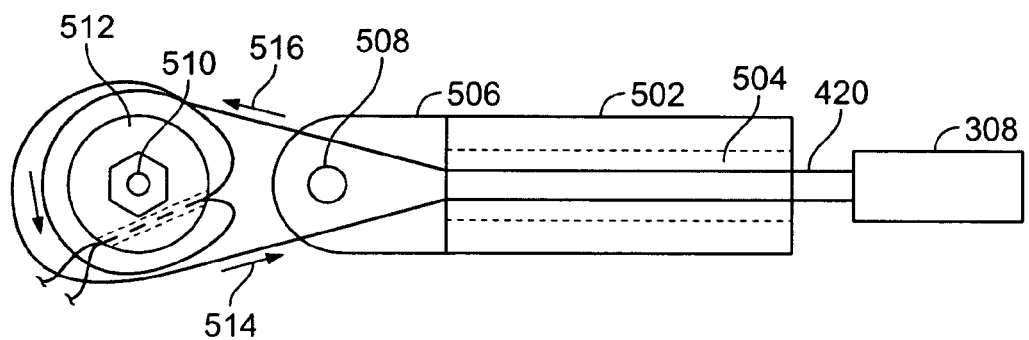
FIG. 5 is an exploded plan view of an exemplary embodiment of an operator end that may be used with the manipulator shown in FIG. 4.
Figure 6:
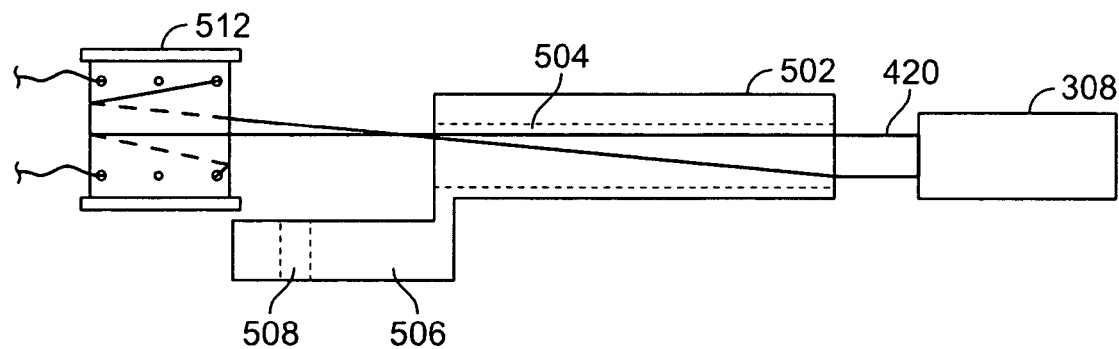
FIG. 6 is a side view of an exemplary embodiment of the operator end shown in FIG. 5.

FIG. 5 is an exploded plan view of an exemplary embodiment of the operator end 308 (shown in FIG. 4). FIG. 6 is a corresponding exploded side view of the exemplary embodiment of the operator end 308 of FIG. 5. Operator end 308 is configured to couple to a handle base 502 that includes a generally cylindrical portion having a bore 504 therethrough. A stepped portion 506 includes a bore 508 therethrough configured to receive a pin 510 (see FIG. 5) about which a handle spool 512 rotates. Control cable 420 is channeled through operator end 308, bore 504 and is wound around spool 512. Handle 320 (not shown in FIG. 5 or FIG. 6) is coupled to spool 512 such that moving handle 320 between first position 414 and second position 416 causes spool 512 to rotate, which in turn feeds control cable 420 in a first direction 514 and takes up control cable 420 in a second direction 516. Moving handle 320 in an opposite direction likewise causes spool 512 to feed and take-up control cable 420 in opposite directions.

Figure 7:
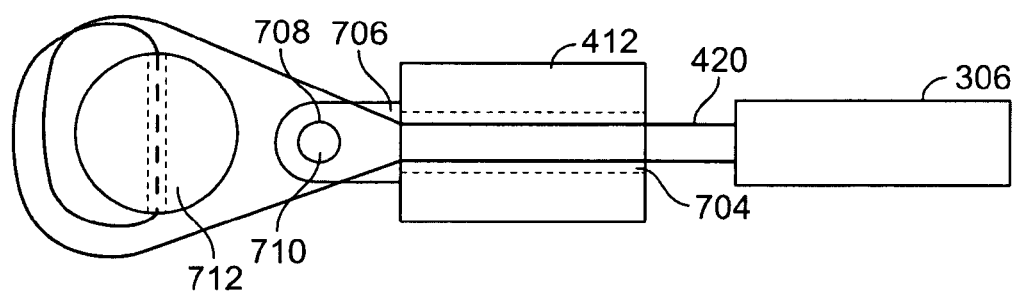
FIG. 7 is an exploded plan view of an exemplary embodiment of the attachment end that may be used with the manipulator shown in FIG. 4.

FIG. 7 is an exploded plan view of an exemplary embodiment of attachment end 412 (shown in FIG. 4). Effector 306 is configured to couple to attachment end 412 that includes a generally cylindrical portion having a bore 704 therethrough. A stepped portion 706 includes a bore 708 therethrough configured to receive a pin 710 about which an effector spool 712 rotates. Control cable 420 is channeled through effector 306, bore 704, and is wound around spool 712. An inspection and/or test tool (not shown in FIG. 5) is releasably coupled to spool 712 such that moving handle 320 between first position 414 and second position 416 causes spool 712 to rotate, which in turn feeds control cable 420 in a first direction 514 and takes up control cable 420 in a second direction. Moving handle 320 in an opposite direction likewise causes spool 512 to feed and take-up control cable 420 in opposite directions.

It will be appreciated that a technical effect of the configurations of the present invention described herein is the remote positioning and operation of test and/or inspection equipment.

The above-described embodiments of a manipulator system provide a cost-effective and reliable means for inspecting and/or servicing equipment. More specifically, the manipulator system includes an effector end and a rotatable attachment end to facilitate positioning a test and/or inspection tool proximate a workpiece, for example, a turbine blade that remains installed on a turbine rotor in an assembled machine, and to facilitate operating the test and/or inspection tool remotely. As a result, the methods and apparatus described herein facilitate testing in a cost-effective and reliable manner.

Exemplary embodiments of manipulator systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A hand-held manipulator comprising:
   a tubular shaft;
   an operator end coupled to said tubular shaft and comprising a first spool rotatably coupled to said operator end;
   an effector comprising an attachment end that includes a second spool rotatably coupled to said attachment end;
   a cable comprising a first end and a second end, said first end slidably coupled within a first aperture defined in said tubular shaft and coupled to said effector, said second end accessible at said operator end;
   at least one inspection device operatively coupled to said second spool such that said at least one inspection device moves with said second spool and is rotatable with said second spool in a first direction away from a center axis of said tubular shaft, and is rotatable away from the center axis in a second direction that is opposite the first direction; and
   a control cable channeled through said shaft from said first spool to said second spool, said control cable wound at least partially around said first spool, said control cable wound at least partially around said second spool such that rotation of said first spool rotates said second spool using said control cable.

2. A manipulator in accordance with claim 1 wherein said effector is coupled to said tubular shaft through a flexible tube.

3. A manipulator in accordance with claim 2 wherein a curvature of said flexible tube defines an angle between said effector and said tubular shaft.

4. A manipulator in accordance with claim 3 wherein shortening said cable changes the angle defined between said effector and said tubular shaft.

5. A manipulator in accordance with claim 1 wherein said at least one inspection device comprises at least one of a borescope, a dye penetrant applicator, an ultrasound probe, a light, a video camera, and an eddy current probe.

6. A manipulator in accordance with claim 1 wherein said effector is configured to pass between a row of circumferentially-spaced vanes to access a row of circumferentially-spaced blades of a rotatable machine.

7. A test and inspection system comprising:
   a hand-held manipulator comprising:
      a tubular shaft coupled to an operator end at a first end and coupled to an effector at a second end opposite said first end, said operator end rotatably coupled to a first spool, said effector rotatably coupled to a second spool;
      a control cable extending slidably through said tubular shaft from said first spool to said second spool, said control cable wound at least partially around said first spool, said control cable wound at least partially around said second spool such that rotation of said first spool rotates said second spool using said control cable,
      a cable comprising a first end and a second end, said first end slidably coupled within a first aperture defined in said tubular shaft and coupled to said effector, said second end accessible at said operator end; and
      an attachment end configured to operatively couple at least one inspection device to said second spool, such that said at least one inspection device moves with said second spool, and is rotatable with said second spool in a first direction away from a center axis of said tubular shaft, and is rotatable away from the center axis in a second direction that is opposite the first direction.

8. A test and inspection system in accordance with claim 7 wherein said at least one inspection device comprises at least one of a borescope, a dye penetrant applicator, an ultrasound probe, a light, a video camera, and an eddy current probe.

9. A test and inspection system in accordance with claim 7 wherein said effector is coupled to said tubular shaft through a flexible tube.

10. A test and inspection system in accordance with claim 9 wherein a curvature of said flexible tube defines an angle between said effector and said tubular shaft.

11. A test and inspection system in accordance with claim 10 wherein shortening said cable changes the angle defined between said effector and said tubular shaft.

12. A test and inspection system in accordance with claim 7 wherein said effector is configured to pass between a row of circumferentially-spaced vanes to access a row of circumferentially-spaced blades of a rotatable machine.

13. A method of machinery testing and inspection using a hand-held manipulator that includes an operator end coupled to a first end of a manipulator body and an attachment end coupled to a second end of the manipulator body, said method comprising:
   inserting a first end of a cable into a first aperture defined in the body first end;
   extending the first end of the cable to a second aperture defined in the attachment end;
   coupling the first end of the cable to the attachment end such that the second end of the cable is accessible at the operator end;
   attaching at least one inspection device to a rotatable spool portion coupled to the attachment end, such that the at least one inspection device moves with the rotatable spool portion;
   positioning the at least one inspection device proximate a component to be inspected; and
   repositioning the at least one inspection device with respect to the component by controlling the operator end of the manipulator.

14. A method in accordance with claim 13 wherein attaching at least one inspection device comprises attaching at least one of a borescope, a dye penetrant applicator, an ultrasound probe, a light, a video camera, and an eddy current probe.

15. A method in accordance with claim 13 wherein attaching at least one inspection device comprises releasably coupling the at least one inspection device to a rotatable spool portion of the attachment end, such that the at least one inspection device moves with the rotatable spool portion.

16. A method in accordance with claim 15 wherein repositioning the at least one inspection device comprises rotating the rotatable spool portion of the attachment end using the operator end.

17. A method in accordance with claim 16 wherein repositioning the at least one inspection device comprises manipulating a handle coupled to the operator end.

18. A method in accordance with claim 17 wherein the operator end handle is coupled to an operator end spool, and wherein repositioning the at least one inspection device comprises linearly translating a control cable through the manipulator body from the operator end spool to the rotatable spool portion of the attachment end wherein the control cable is wound at least partially around the operator end spool and wound at least partially around the attachment end spool portion such that rotation of the operator end spool to the rotates the attachment end spool.

19. A method in accordance with claim 13 wherein the manipulator body includes a first tubular portion coupled to a first end of a flexible portion and an effector coupled to a second end of the flexible portion, and wherein the first tubular portion and the effector are coupled through the flexible portion using the cable, said method further comprising withdrawing the cable from the first tubular portion to change the position of the effector with respect to the component.

20. A method in accordance with claim 19 wherein a curvature of the flexible portion defines an angle between the first tubular portion and the effector and wherein withdrawing the cable from the first tubular portion comprises changing the angle defined between the first tubular portion and the effector.

* * * * *